(12) United States Patent
Gelbein

(10) Patent No.: US 6,337,412 B1
(45) Date of Patent: Jan. 8, 2002

(54) THREE STAGE PROPYLENE OXIDE PROCESS

(75) Inventor: Abraham P. Gelbein, Falls Church, VA (US)

(73) Assignee: Chemical Research & Licensing Company, Pasadena, TX (US)

( * ) Notice: Subject to any disclaimer, the term of this patent is extended or adjusted under 35 U.S.C. 154(b) by 0 days.

(21) Appl. No.: 09/841,427

(22) Filed: Apr. 24, 2001

Related U.S. Application Data

(60) Provisional application No. 60/199,564, filed on Apr. 25, 2000.

(51) Int. Cl.[7] .................. C07D 301/12; C07D 303/04; B01D 3/36
(52) U.S. Cl. ......................................... 549/531; 203/38
(58) Field of Search ............................ 549/531; 203/38

(56) References Cited

U.S. PATENT DOCUMENTS

| | | |
|---|---|---|
| 3,350,422 A | 10/1967 | Kollar |
| 4,113,747 A | 9/1978 | Prescher et al. |
| 4,137,242 A | 1/1979 | Prescher et al. |
| RE30,945 E | 5/1982 | Prescher et al. |
| RE31,381 E | 9/1983 | Prescher et al. |
| 5,523,426 A | 6/1996 | Jubin et al. |
| 5,874,017 A | 2/1999 | Palmer et al. |
| 5,892,066 A | 4/1999 | Grey |
| 5,912,367 A | 6/1999 | Chang |
| 5,965,754 A | 10/1999 | Clark et al. |
| 5,973,171 A | 10/1999 | Cochran et al. |
| 6,008,389 A | 12/1999 | Grosch et al. |
| 6,031,116 A | 2/2000 | Bowman et al. |
| 6,066,750 A | 5/2000 | Chang |
| 6,080,894 A | 6/2000 | Oyague et al. |
| 6,096,910 A | 8/2000 | Yamamoto et al. |
| 6,160,137 A | 12/2000 | Tsuji et al. |

Primary Examiner—Robert W. Ramsuer
Assistant Examiner—Kamal Saeed
(74) Attorney, Agent, or Firm—Kenneth H. Johnson

(57) ABSTRACT

A three stage process for producing propylene oxide from propylene, oxygen, and hydrogen. The first reaction step is the oxidation of isopropanol/water with molecular oxygen in a reaction-distillation column (approx. 500 psi and 350° F.), to produce hydrogen peroxide and acetone. The column is configured with an upper high liquid holdup reaction zone and a lower short residence time stripping zone. Inert gas circulating through the column effects separation of the hydrogen peroxide as part of the bottoms fraction and acetone as part of the distillate fraction. The liquid part of the distillate fraction comprising acetone, isopropanol and water is then reacted with hydrogen (second reaction step) under reactive-distillation conditions to convert the contained acetone back to isopropanol for subsequent recycle to the first reaction step. The third reaction step is the epoxidation of propylene (in stoichiometric excess) with the hydrogen peroxide solution in the presence of a titanium silicalite catalyst. The reaction is performed in a series of fixed bed adiabatic reactors with intercooling. Product separation is by conventional distillation. Unreacted propylene is recycled to the epoxidation step and water/isopropanol to the first reaction step.

7 Claims, 2 Drawing Sheets

THREE STAGE PROPYLENE OXIDE PROCESS

This application the benefit of U.S. provisional application No. 60/199,564 filed on Apr. 25, 2000.

BACKGROUND OF THE INVENTION

1. Field of the Invention

The present invention relates to a process for the industrial production of propylene oxide by the reaction of propylene with hydrogen peroxide.

2. Related Information

Three routes to propylene oxide (PO) are currently practiced commercially. The oldest art involves the intermediate formation of propylene chlorohydrin by reacting propylene with $Cl_2/H_2O$ followed by hydrolysis with lime to release the PO and capture the $Cl_2$ as $CaCl_2$. This process is no longer practiced in the U.S. because of the high cost of disposal of the waste $CaCl_2$. An alternative is to use NaOH as the base and to recycle the Na and Cl values by integrating the process with a caustic/chlorine plant:

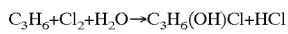

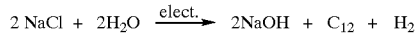

Net::

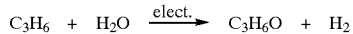

The more recent technologies involve the catalytic oxidation of propylene with t-butyl hydroperoxide (a tertiary hydroperoxide) or β-phenethyl hydroperoxide (a secondary hydroperoxide) to produce PO and co-product alcohols. The hydroperoxides are obtained by catalytic oxidation of isobutane and ethylbenzene respectively:

$$(CH_3)_3CH+O_2 \rightarrow (CH_3)_3COOH$$

$$(CH_3)_3COOH+C_3H_6 \rightarrow C_3H_6O+(CH_3)_3COH$$

and $$(C_6H_5)CH_2CH_3+O_2(C_6H_5)CH(OOH)CH_3(C_6H_5)CH(OOH)CH_3+$$
$$CH_3H_6 \rightarrow CH_3H_6O+(C_6H_5)CH(OH)CH_3$$

The process economics for these routes are highly dependent on the value of the coproduct alcohols. The first route is practiced by ARCO and Texaco to produce PO and methyl-t-butyl ether wherein the t-butanol (or isobutylene derived from the alcohol) reacts with methanol to produce the ether. Varients of the second route are practiced by Shell and ARCO to produce PO and styrene by dehydrating the β-phenethyl alcohol.

$$(CH_3)_3COH+CH_3OH \rightarrow CH_3OC(CH_3)_3+H_2O$$

$$(C_6H_5)CH(OH)CH_3 \rightarrow (C_6H_5)CH=CH_2+H_2O$$

The search for a single product-direct vapor phase oxidation technology to PO using molecular oxygen continues to be a principal interest of the chemical industry. It is well known that propylene and an active oxygen species such as hydrogen peroxide or an organic hydroperoxide will react over a titanium silicate catalyst, for example as to produce high yields of propylene oxide as shown in U.S. Pat. Nos. 4,833,260 and 4,367,342 which are incorporated herein. In spite of much effort, a catalyst system that gives high selectivity and practical conversion and catalyst life is yet to be developed. For example a recent patent, U.S. Pat. No. 6,031,116 employs a titanium silicalite (TS-1) supported gold catalyst. The highest per pass conversion reported in the cited examples is 0.87 mol % at 92 mol % selectivity to PO. Other examples show that selectivity is in inverse relationship to conversion.

Another single product approach to PO that has been the subject of old and recent art is to oxidize propylene with hydrogen peroxide in a liquid phase in the presence of a titanium silicalite catalyst.

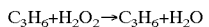

The hydrogen peroxide is produced by reacting oxygen with a secondary alcohol:

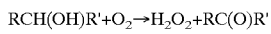

The coproduct ketone is subsequently reacted with $H_2$ to return the alcohol. The overall net reaction is:

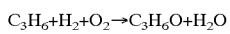

Such a process is described in U.S. Pat. No. 5,523,426 which is incorporated herein. The process disclosed is an integrated epoxidation process of:

(a) reacting a $C_3$–$C_4$ secondary alcohol and molecular oxygen in a liquid phase to form an oxidant mixture comprised of the $C_3$–$C_4$ secondary alcohol, a $C_3$–$C_4$ aliphatic ketone corresponding to the $C_3$–$C_4$ secondary alcohol, and hydrogen peroxide;

(b) separating substantially all of the $C_3$–$C_4$ secondary ketone from the oxidant mixture to provide a concentrated hydrogen peroxide-containing stream comprised of $C_3$–$C_4$ secondary alcohol, hydrogen peroxide, and less than 1 weight percent $C_3$–$C_4$ ketone;

(c) reacting the concentrated hydrogen peroxide-containing stream with a $C_2$–$C_4$ olefin in the presence of a titanium silicalite catalyst and a diluent to form an epoxidation reaction mixture comprised of a $C_2$–$C_4$ epoxide corresponding to the $C_2$–$C_4$ olefin, water, and $C_3$–$C_4$ secondary alcohol;

(d) separating substantially all of the $C_2$–$C_4$ epoxide from the epoxidation reaction mixture to form a crude alcohol stream comprised of water, the $C_3$–$C_4$ secondary alcohol, and less than 1 weight percent of the $C_2$–$C_4$ epoxide; and (e) recycling at least a portion of the crude alcohol stream for use as at least a portion of the diluent in step (c).

SUMMARY OF THE INVENTION

Briefly the present invention discloses an integrated process for the production of propylene oxide comprising:

(a) Reacting isopropanol with oxygen under conditions effective to produce a first reaction product comprising hydrogen peroxide and acetone;

(b) separating and recovering said hydrogen peroxide from said first reaction product;

(c) separating and recovering said acetone from said first reaction product;

(d) reacting said acetone with hydrogen under conditions effective to produce isopropanol;

(e) recycling said isopropanol of step (d) to step (a);

(f) reacting said hydrogen peroxide of step (b) with propylene under conditions effective to produce a second reaction product comprising propylene oxide isopropanol and unreacted propylene;

(g) recovering said second reaction product;

(h) separating and recovering said propylene oxide from said second reaction product;

(i) separating and recovering said isopropanol from said second reaction product and recycling said isopropanol to step (a); and (j) separating and recovering said propylene from said second reaction product and recycling said propylene to step (f).

DETAILED DESCRIPTION

The present process is also an integrated epoxidation process in which the hydrogen peroxide is produced via an isopropanol-acetone cycle. It incorporates innovations in the method used for generating the hydrogen peroxide and hydrogenating the acetone and is unique in at least the following respects:

(a) The hydrogen peroxide forming reaction is carried out in a reaction/distillation column wherein a concentrated hydrogen peroxide solution in primarily water-isopropanol is directly obtained as the bottoms product and water-isopropanol-acetone as an overhead vapor product.

(b) The acetone concentration in the hydrogen peroxide solution of (a) is between 1–2 wt %.

(c) The crude alcohol stream obtained after propylene oxide separation is not recycled as diluent to the epoxidation reactor.

(d) Acetone produced in (a) is not separated from the water-isopropanol prior to hydrogenation which is conducted under catalytic distillation conditions.

Figure 1:
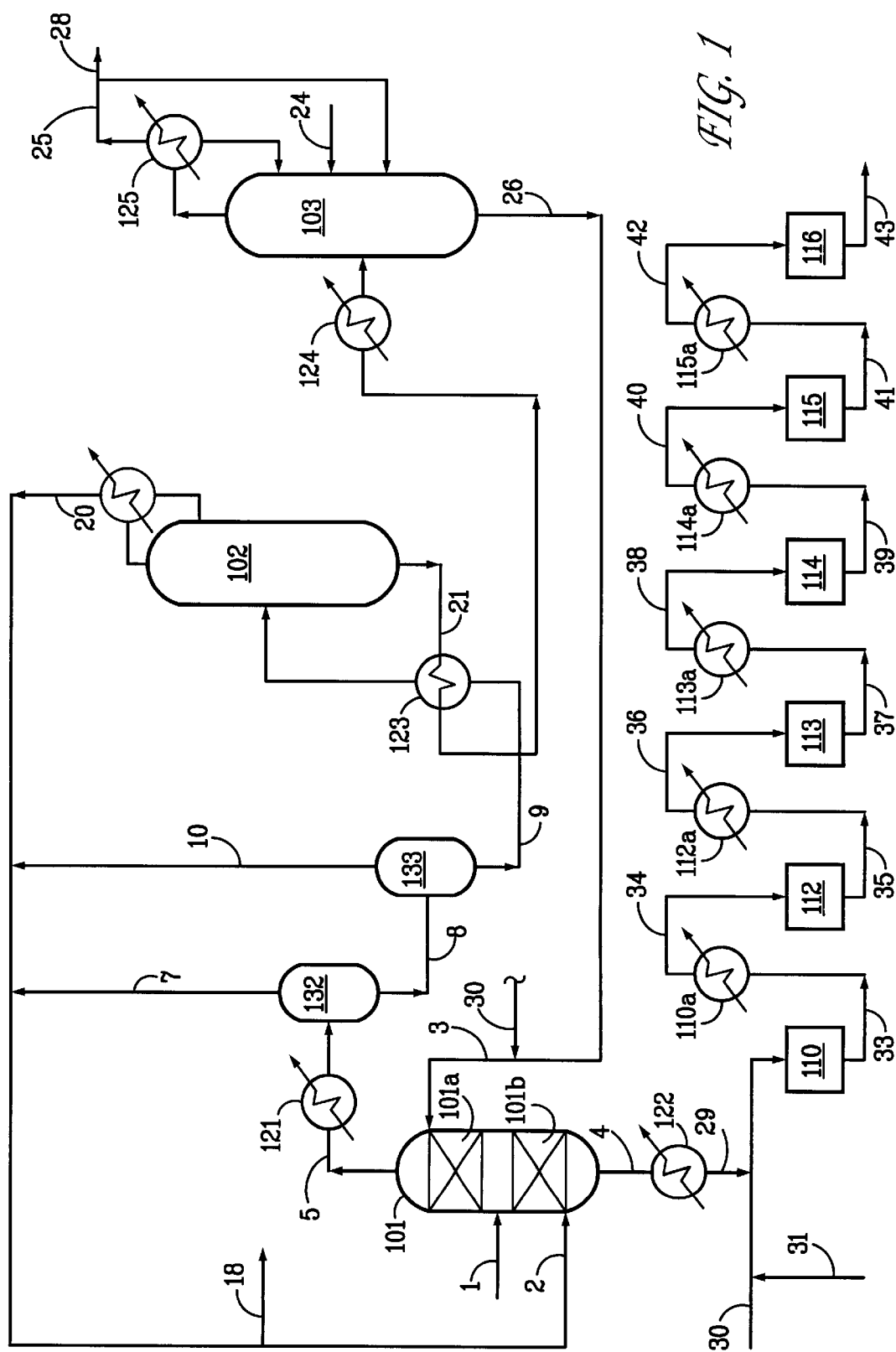
FIG. 1 depicts the present process through the epoxidation reaction.
Figure 2:
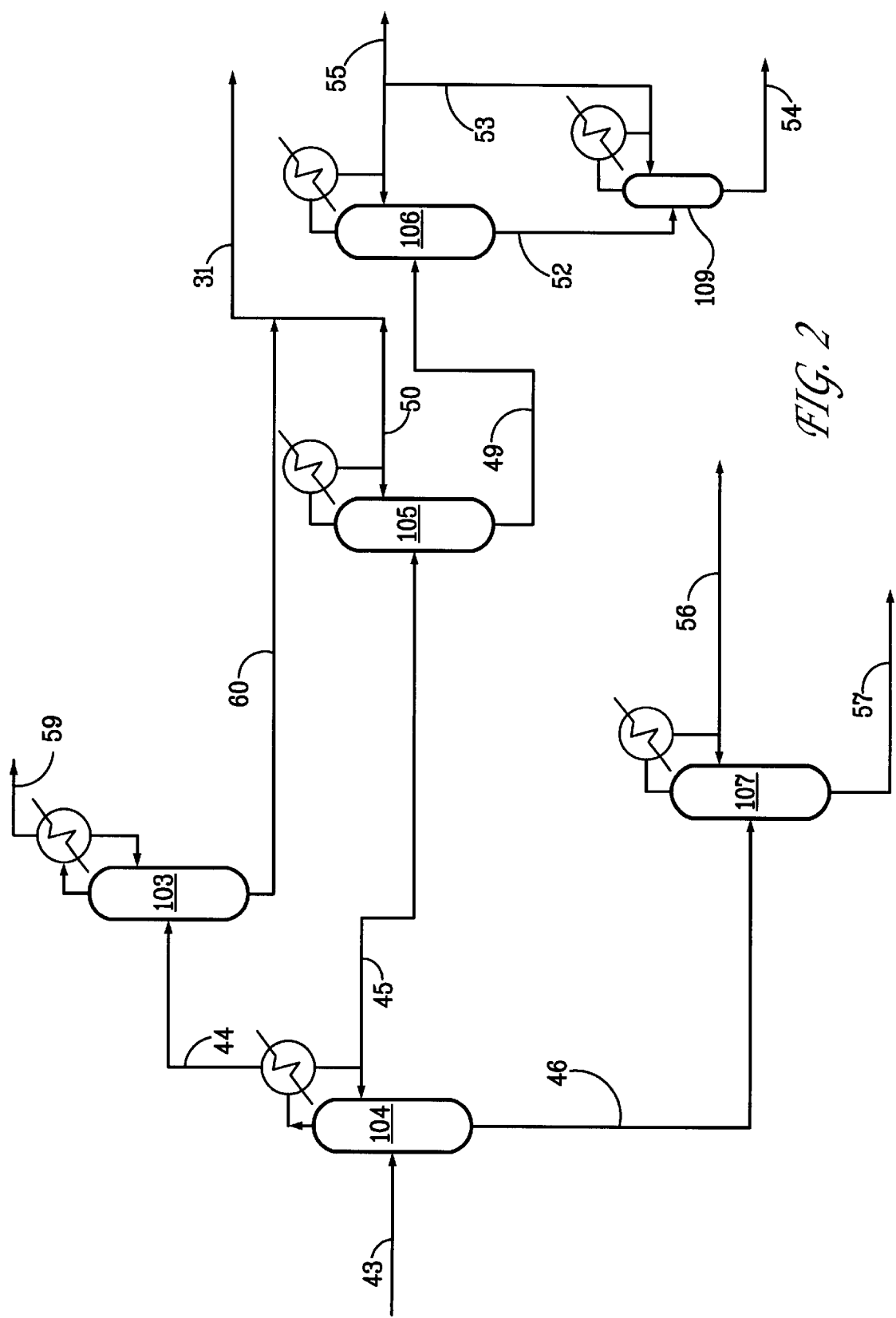
FIG. 2 depicts the product recovery section of the process.

The process is described with reference to FIGS. 1 and 2. The process represents a plant producing 400 MM lb/yr propylene oxide. Feed propylene is assumed to be free of propane. Stream data are reported in Stream Table. Hydrogen peroxide is produced in multistage reaction-distillation column 101 operating at 500 psi using oxygen as the oxidant. A small amount of isopropanol is oxidized to acetic acid as:

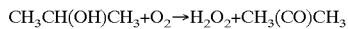

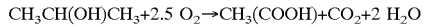

The column is configured with an upper zone 101a containing ten high liquid holdup reaction-distillation stages, a lower zone 101b containing twenty low liquid holdup distillation stages, and a reboiler. After startup the isopropanol is recycled from downstream as described later with makeup isopropanol being added via line 3a. Recycle isopropanol-water is fed via line 3 on the top stage of the column, oxygen vapor is fed via line 1 into the vapor space above stage ten (top of column is stage 1), and recycle gas is fed via line 2 into the liquid in the reboiler. Operating conditions have been selected so that:

(a) vapor phase oxygen concentration at any point in the column is outside the flammability envelope for oxygen-hydrocarbon mixtures (<10 vol % 02), (b) partial pressure of oxygen above stage 10 is ~30 psi, (c) reboiler temperature is <200° C. (392° F.), Certain inorganic salts (e.g., alkali metal salts of an oxy acid of phosphorus) are present at ppm levels to the system to stabilize the hydrogen peroxide product. Bottoms liquid product in line 4 contains essentially all of the hydrogen peroxide product, about 20% of the isopropanol and water fed to the column, 3.5% of the acetone produced in the column, essentially all of the acetic acid byproduct, trace amounts of dissolved gases, and the inorganic stabilizer(s) added to the system. Hydrogen peroxide concentration is ~29 wt %. Stream 4 is cooled in heat exchanger 122 and flows to the epoxidation reaction system described below via line 29.

Overhead stream 5 from column 101 is partially condensed at column pressure in condenser 121 and phases separated in tank 132. The vapor fraction in line 7 comprising most of the noncondensibles (diluent $N_2$, unreacted $O_2$, $CO_2$) is compressed, combined with vapor stream 20 (obtained as noted below) and recycled to column 101 via line 2 after removal of purge stream 18 which contains most of the net make of $CO_2$. The liquid fraction from tank 132 consisting of a water/isopropanol azeotrope, acetone, and a trace of $H_2O_2$ is fed via line 8 to tank 133 where it is flashed at ~150 psi, phase separated with the vapor fraction removed via line 10. The bottom fraction from tank 133 is fed via line 9 and stripped in column 102 to remove residual $N_2$, $O_2$, and $CO_2$ as vapor distillate via line 20. The latter is combined with vapor fraction 10, compressed and recycled to column 101 via line 2 as noted above. Bottoms product from column 102 flows via line 21 to catalytic distillation column 103 via feed effluent exchanger 123 and cooler 124 is fed to the top stage of column 103 (stage two; condenser is stage one) which is configured with an upper catalytic distillation zone (ten theoretical distillation stages), a lower distillation zone (forty theoretical stages) and partial condenser 125 operating with total liquid reflux. Purge line 28 is provide to prevent the buildup of byproducts. Column head pressure in column 103 is ~150 psi. Hydrogen is fed via line 24 together with recycle hydrogen from line 25 to the column above stage 11. 99% conversion of the acetone to isopropanol is achieved. Isopropanol is recovered in line 26 and recycled to reactor 10 through line 3.

Epoxidation is conducted in a cascade of six fixed bed adiabatic reactors (110 to 116) with intercoolers (110a to 115a) to remove the heat of reaction. Inlet temperature to a reactor is 120° F. and maximum adiabatic temperature rise ~70° F. Pressure to the cascade is ~350 psi with a 10 psi drop is across each reactor. Feed to the cascade is comprised of the hydrogen peroxide solution from line 29, which is cooled by the bottoms from reactor 101 in heat exchanger 122, propylene feed line 30, and recycle propylene line 31. Acetone and propylene glycol are produced as by-products:

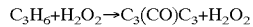

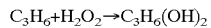

The product from reactor 110–115 passes through cooler 110a–115a, via line 33–34, line 35–36, 37–38, 39–40 and 41–42, respectively. The epoxidation reaction product line 43 contains propylene oxide, water, isopropanol, propylene, acetone, propylene glycol, trace amounts of dissolved gases ($N_2$, $O_2$, $CO_2$), and stabilizer additives. First step in the product recovery train is splitting of the components in column 104 into a distillate fraction (line 44+line 45) containing the PO, propylene, and gases (a small part of the acetone and water) and a bottoms fraction line 46 containing the water, isopropanol, acetone, glycol, and additives which is further distilled in column 107 as described below. The distillate is partially condensed to separate the gases together with some propylene as vapor in line 44 which is subsequently distilled in column 108 under cryogenic conditions to recover the propylene in line 60 for recycle via line 31 and discharge the gases via line 59 to a flare system (not shown). The gases will include some oxygen so it may be necessary to hydrotreat (not shown) line 44 material prior to distillation to reduce the oxygen concentration to a level sufficient to avoid flammability problems in the distillation. The liquid distillate fraction in line 45 is sent to the propylene column 105 where propylene is recovered as liquid overhead in line 48 and crude PO (contains a small amount of acetone and water) as the bottoms product via line 49. 99.9+% PO is obtained at line 55 as the combined distillate product from the primary 106 and secondary 109 PO columns. The recovered water and acetone is recycled via line 54 to the acetone hydrogenation column 103.

Column 107 is the isopropanol/water azeotrope column. The azeotrope is recovered as distillate in line 56 and is recycled to the oxidation reactor 101. The bottoms product in line 57 which contains the net water produced in the system, heavy organic by-products (acetic acid, glycol) produced in the system and additives is sent to waste treatment (not shown).

STREAM TABLE

| | 1 | 2 | 3 | 4 | 5 | 7 | 8 | 9 | 10 | 18 | 20 |
|---|---|---|---|---|---|---|---|---|---|---|---|
| Temperature F. | 300 | 312 | 240 | 382.4 | 344 | 120 | 120 | 119.4 | 119.4 | 166.9 | 188.1 |
| Pressure PSI | 530 | 524 | 500 | 520 | 500 | 500 | 500 | 150 | 150 | 520 | 150 |
| Vapor Frac | 1 | 1 | 0 | 0 | 1 | 1 | 0 | 0 | 1 | 1 | 1 |
| Mole Flow LBMOL/HR | 1075 | 10325 | 11082.6 | 2978.297 | 19514.51 | 9238.096 | 10276.414 | 9835.635 | 440.779 | 38.875 | 635 |
| Mass Flow LB/HR | 34398.71 | 323630.629 | 511052.878 | 119468.718 | 749613.499 | 281056.363 | 468557.136 | 453571.706 | 14985.43 | 1219.142 | 27407.392 |
| Volume Flow CUFT/HR | 16535.38 | 163172.472 | 11661.591 | 2777.117 | 336587.25 | 1149344.368 | 9591.349 | 9184.902 | 18261.69 | 502.649 | 29426.753 |
| Enthalpy MMBTU/HR | 1.704 | −293.86 | −1391.555 | −305.816 | −1259.895 | −199.904 | −1284.315 | −1259.486 | −24.829 | −1.156 | −85.155 |
| Mole Flow LBMOL/HR | | | | | | | | | | | |
| O2 | 1075 | 491.135 | 0 | 1.322 | 492.993 | 467.195 | 25.798 | 6.624 | 19.174 | 1.858 | 6.624 |
| N2 | 0 | 7901.878 | 0 | 20.299 | 7881.579 | 7536.714 | 344.865 | 76.726 | 268.139 | 29.707 | 76.727 |
| C3- | 0 | 0 | 7400 | 0 | 0 | 0 | 0 | 0 | 0 | 0 | 0 |
| IC3OH | 0 | 80.468 | 0 | 1106.404 | 5332.868 | 36.159 | 5296.708 | 5290.862 | 5.846 | 0.304 | 38.766 |
| H2O2 | 0 | 0.001 | 0 | 1017.032 | 3.75 | 0.001 | 3.75 | 3.749 | 0 | 0 | 0 |
| Acetone | 0 | 96.214 | 0 | 38.742 | 1078.253 | 38.513 | 1039.741 | 1033.367 | 6.373 | 0.364 | 51.691 |
| ACOH | 0 | 0 | 0 | 20.175 | 0.241 | 0 | 0.241 | 0.241 | 0 | 0 | 0 |
| HCOOH | 0 | 0 | 0 | 0 | 0 | 0 | 0 | 0 | 0 | 0 | 0 |
| H2O | 0 | 43.037 | 3682.6 | 760.395 | 3006.073 | 17.803 | 2988.27 | 2985.295 | 2.975 | 0.163 | 22.421 |
| PROPA-01 | 0 | 0 | 0 | 0 | 0 | 0 | 0 | 0 | 0 | 0 | 0 |
| PO | 0 | 0 | 0 | 0 | 0 | 0 | 0 | 0 | 0 | 0 | 0 |
| H2 | 0 | 0 | 0 | 0 | 0 | 0 | 0 | a | 0 | 0 | 0 |
| N-PEN-01 | 0 | 0 | 0 | 0 | 0 | 0 | 0 | 0 | 0 | 0 | 0 |
| CO2 | 0 | 1712.266 | 0 | 13.928 | 1718.753 | 1141.712 | 577.041 | 438.77 | 138.271 | 6.478 | 438.77 |

| | 21 | 24 | 25 | 26 | 28 | 29 | 30 | 31 | 33 | 34 | 35 |
|---|---|---|---|---|---|---|---|---|---|---|---|
| Temperature F. | 302.8 | 110 | 135.7 | 311.1 | 135 | 120 | 120 | 120 | 193.3 | 120 | 193.1 |
| Pressure PSI | 151 | 155 | 149 | 154 | 155 | 348 | 348 | 348 | 338 | 325 | 327 |
| Vapor Frac | 0 | 1 | 1 | 0 | 0.998 | 0 | 0 | 0 | 0.175 | 0 | 0.127 |
| Mole Flow LBMOL/HR | 9200.636 | 974.30 | 2230 | 9204.187 | 2230 | 2978.297 | 3985 | 1015 | 7970.708 | 7970.708 | 7963.505 |
| Mass Flow LB/HR | 426164.481 | 1964.086 | 9613.399 | 428119.495 | 960.4327 | 119468.718 | 167691.35 | 42711.85 | 329871.918 | 329871.918 | 329871.918 |
| Volume Flow CUFT/HR | 10606.627 | 38427.674 | 95623.503 | 10761.872 | 91617.428 | 2117.664 | 5826.201 | 1483.963 | 36599.417 | 8698.597 | 29742.666 |
| Enthalpy MMBTU/HR | −1100.061 | 0.221 | −10.53 | −1124.958 | −10.605 | −333.635 | 16.148 | 4.113 | −313.574 | −345.752 | −345.752 |
| Mole Flow LBMOL/HR | | | | | | | | | | | |
| O2 | 0 | 0 | 0 | 0 | 0 | 1.322 | 0 | 0 | 1.322 | 1.322 | 1.322 |
| N2 | 0 | 0 | 0 | 0 | 0 | 20.299 | 0 | 0 | 20.299 | 20.299 | 20.299 |
| C3- | 5252.098 | 0 | 0 | 6222.733 | 51.6 | 1106.404 | 3985 | 1015 | 4678.924 | 4678.924 | 4374.193 |
| IC3OH | 0 | 0 | 51.722 | 0 | 0 | 1017.032 | 0 | 0 | 695.955 | 1106.404 | 1106.404 |
| H2O2 | 3.749 | 0 | 0 | 0 | 0 | 0 | 0 | 0 | 0 | 0 | 0 |
| Acetone | 981.678 | 0 | 30.558 | 10.902 | 30.539 | 38.742 | 0 | 0 | 59.651 | 59.955 | 79.496 |
| ACOH | 0.241 | 0 | 0 | 0.241 | 0 | 20.175 | 0 | 0 | 20.175 | 20.175 | 20.175 |
| HCOOH | 0 | 0 | 0 | 0 | 0 | 0 | 0 | 0 | 0 | 0 | 0 |
| H2O | 2962.87 | 0 | 25.049 | 2970.311 | 24.991 | 760.395 | 0 | 0 | 1073.882 | 1073.882 | 1371.41 |
| PROPA-01 | 0 | 0 | 0 | 0 | 0 | 0 | 0 | 0 | 7.59 | 7.59 | 14.793 |
| PO | 0 | 0 | 0 | 0 | 0 | 0 | 0 | 0 | 292.578 | 292.578 | 570.26 |
| H2 | 0 | 974.307 | 2122.671 | 0 | 2122.87 | 0 | 0 | a | 0 | 0 | 0 |
| N-PEN-01 | 0 | 0 | 0 | 0 | 0 | 0 | 0 | 0 | 0 | 0 | 0 |
| CO2 | 0 | 0 | 0 | 0 | 0 | 13.928 | 0 | 0 | 13.928 | 13.928 | 13.928 |

-continued

STREAM TABLE

| | 36 | 37 | 38 | 39 | 40 | 41 | 42 | 43 | 44 | 45 | 46 |
|---|---|---|---|---|---|---|---|---|---|---|---|
| Temperature F. | 120 | 188.1 | 120 | 155.9 | 120 | 129.2 | 120 | 123 | 108.6 | 108.6 | 348.9 |
| Pressure PSI | 305 | 316 | 290 | 305 | 304 | 294 | 293 | 283 | 245 | 245 | 250 |
| Vapor Frac | 0 | 0.044 | 0 | 0 | 0 | 0 | 0 | 0 | 1 | 0 | 0. |
| Mole Flow LBMOL/HR | 7963.505 | 7957.775 | 7957.775 | 7955.185 | 7955.185 | 7954.563 | 7954.583 | 7954.362 | 99.46 | 4873.54 | 2981.362 |
| Mass Flow LB/HR | 329871.918 | 329871.918 | 329871.918 | 329871.918 | 329871.918 | 329871.918 | 329871.918 | 329871.918 | 4054.298 | 219548.513 | 106269.108 |
| Volume Flow CUFT/HR | 8612.235 | 16620.276 | 8543.406 | 8981.876 | 8512.261 | 8615.768 | 8504.775 | 8537.961 | 2475.827 | 6544.506 | 2655.205 |
| Enthalpy MMBTU/HR | −376.523 | −376.523 | −400.973 | −400.973 | −412.014 | −412.014 | −414.665 | −414.665 | 0.449 | −38.152 | −355.535 |
| Mole Flow LBMOL/HR | | | | | | | | | | | |
| O2 | 1.322 | 1.322 | 1.322 | 1.322 | 1.322 | 1.322 | 1.322 | 1.322 | 0.674 | 0.648 | 0 |
| N2 | 20.299 | 20.299 | 20.299 | 20.299 | 20.299 | 20.299 | 20.299 | 20.299 | 11.349 | 8.951 | 0 |
| C3- | 4374.193 | 4131.784 | 4131.784 | 4022.235 | 4022.235 | 3995.915 | 3995.915 | 3987.427 | 84.047 | 3903.38 | 0 |
| IC3OH | 1108.404 | 1106.404 | 1106.404 | 1106.404 | 1106.404 | 1106.404 | 1106.404 | 1106.404 | 0 | 0 | 1106.404 |
| H2O2 | 391.225 | 148.815 | 148.815 | 39.266 | 39.266 | 12.947 | 12.947 | 4.459 | 0 | 0 | 4.459 |
| Acetone | 79.496 | 95.282 | 95.282 | 102.416 | 102.416 | 104.13 | 104.13 | 104.683 | 0.022 | 12.661 | 92 |
| ACOH | 20.175 | 20.175 | 20.175 | 20.175 | 20.175 | 20.175 | 20.175 | 20.175 | 0 | 0 | 20.175 |
| HCOOH | 0 | 0 | 0 | 0 | 0 | 0 | 0 | 0 | 0 | 0 | 0 |
| H2O | 1371.41 | 1608.089 | 1608.089 | 1715.048 | 1715.048 | 1740.746 | 1740.746 | 1749.033 | 0.002 | 14.774 | 1734.257 |
| PROPA-01 | 14.793 | 20.253 | 20.523 | 23.112 | 23.112 | 23.734 | 23.734 | 23.935 | 0 | 0 | 23.935 |
| PO | 570.28 | 791.153 | 791.153 | 890.979 | 890.979 | 914.962 | 914.962 | 922.697 | 2.033 | 920.531 | 0.133 |
| H2 | 0 | 0 | 0 | 0 | 0 | 0 | 0 | 0 | 0 | 0 | 0 |
| N-PEN-01 | 0 | 0 | 0 | 0 | 0 | 0 | 0 | 0 | 1.333 | 0 | 0 |
| CO2 | 13.928 | 13.928 | 13.928 | 13.928 | 13.928 | 13.928 | 13.928 | 13.928 | 1.333 | 12.596 | 0 |

| | 49 | 50 | 52 | 53 | 54 | 55 | 56 | 57 | 59 | 60 | |
|---|---|---|---|---|---|---|---|---|---|---|---|
| Temperature F. | 296.5 | 94.5 | 181.7 | 150.5 | 185.1 | 150.4 | 233.8 | 286 | 41.3 | 107.1 | |
| Pressure PSI | 255 | 350 | 55 | 40 | 41 | 40 | 50 | 52 | 243 | 244 | |
| Vapor Frac | 0 | 0 | 0 | 0 | 0 | 0.044 | 0 | 0 | 1 | 0 | |
| Mole Flow LBMOL/HR | 947.298 | 3926.242 | 67.298 | 39 | 28.298 | 919 | 1989.331 | 992.031 | 22 | 77.46 | |
| Mass Flow LB/HR | 54427.193 | 165121.32 | 3354.658 | 2260.921 | 1093.735 | 53333.457 | 86067.822 | 20181.286 | 761.902 | 3292.396 | |
| Volume Flow CUFT/HR | 1403.933 | 5403.802 | 72.019 | 47.438 | 23.256 | 7753.98 | 1934.694 | 370.182 | 486.723 | 108.837 | |
| Enthalpy MMBTU/HR | −43.373 | 9.813 | −4.961 | −1.956 | −3.068 | −45.525 | −246.426 | −121.23 | −0.16 | 0.161 | |
| Mole Flow LBMOL/HR | | | | | | | | | | | |
| O2 | 0 | 0.648 | 0 | 0 | 0 | 0 | 0 | 0 | 0.674 | 0 | |
| N2 | 0 | 8.951 | 0 | 0 | 0 | 0 | 0 | 0 | 11.349 | 0 | |
| C3- | 0 | 3903.38 | 0 | 0 | 0 | 0 | 0 | 0 | 8.644 | 75.403 | |
| IC3OH | 0 | 0 | 0 | 0 | 0 | 0 | 1106.404 | 0 | 0 | 0 | |
| H2O2 | 12.661 | 0 | 12.661 | 0.006 | 12.655 | 0.006 | 0 | 4.459 | 0 | 0.022 | |
| Acetone | 0 | 0 | 0 | 0 | 0 | 0 | 92 | 20.175 | 0 | 0 | |
| ACOH | 14.774 | 0 | 13.828 | 0.105 | 13.723 | 1.051 | a | 0 | 0 | 0.002 | |
| HCOOH | 0 | 0 | 0 | 0 | 0 | 0 | 790.795 | 943.463 | 0 | 0 | |
| H2O | 919.863 | 0.668 | 040.809 | 038.889 | 1.92 | 917.943 | 0.133 | 23.935 | 0 | 2.033 | |
| PROPA-01 | 0 | 0 | 0 | 0 | 0 | 0 | 0 | 0 | 0 | 0 | |
| PO | 0 | 0 | 0 | 0 | 0 | 0 | 0 | 0 | 0 | 0 | |
| H2 | 0 | 0 | 0 | 0 | 0 | 0 | 0 | 0 | 0 | 0 | |
| N-PEN-01 | 0 | 12.596 | 0 | 0 | 0 | 0 | 0 | 0 | 1.333 | 0 | |
| CO2 | | | | | | | | | | | |

The invention claimed is:

1. An integrated process for the production of propylene oxide comprising:
   (a) Reacting isopropanol with oxygen under conditions effective to produce a first reaction product comprising hydrogen peroxide and acetone;
   (b) separating and recovering said hydrogen peroxide from said first reaction product;
   (c) separating and recovering said acetone from said first reaction product;
   (d) reacting said acetone with hydrogen under conditions effective to produce isopropanol;
   (e) recycling said isopropanol of step (d) to step (a);
   (f) reacting said hydrogen peroxide of step (b) with propylene under conditions effective to produce a second reaction product comprising propylene oxide, isopropanol and unreacted propylene;
   (g) recovering said second reaction product;
   (h) separating and recovering said propylene oxide from said second reaction product;
   (i) separating and recovering said isopropanol from said second reaction product and recycling said isopropanol to step (a); and
   (j) separating and recovering said propylene from said second reaction product and recycling said propylene to step (f).

2. The process according to claim 1 wherein steps (a), (b) and (c) are carried out concurrently by reaction and fractional distillation in reaction distillation zone.

3. The process according to claim 1 wherein step (d) is carried out to concurrently react hydrogen with acetone and to separate product isopropanol by reaction and fractional distillation in a reaction distillation zone.

4. The process according to claim 1 wherein step (f) is carried out in a plurality of reaction stages with cooling between stages.

5. The process according to claim 2 wherein step (d) is carried out to concurrently react hydrogen with acetone and to separate product isopropanol by reaction and distillation in a reaction distillation zone.

6. The process according to claim 5 wherein step (f) is carried out in a plurality of reaction stages with cooling between stages.

7. An integrated process for the production of propylene oxide comprising:
   (a) concurrently in reaction distillation zone:
      (i) reacting isopropanol with oxygen under conditions effective to produce a first reaction product comprising hydrogen peroxide, acetone and unreacted isopropanol;
      (ii) separating and recovering said hydrogen peroxide from said acetone and isopropanol by fractional distillation;
   (b) separating said acetone from said unreacted isopropanol by fractional distillation
   (c) recycling said unreacted isopropanol to step (a);
   (d) concurrently in a reaction distillation zone:
      (i) reacting hydrogen with acetone under conditions effective to produce isopropanol and
      (ii) separating isopropanol by fractional distillation;
   (e) recycling said isopropanol of step (d) to step (a);
   (f) reacting said hydrogen peroxide of step (b) with propylene in at least two serial reactions with cooling therebetween under conditions effective to produce a second reaction product comprising propylene oxide, isopropanol and unreacted propylene;
   (g) recovering said second reaction product by fractional distillation;
   (h) separating and recovering said propylene oxide from said second reaction product by fractional distillation;
   (i) separating and recovering said isopropanol from said second reaction product and recycling said isopropanol to step (a); and
   (j) separating and recovering said propylene from said second reaction product and recycling said propylene to step (f).

* * * * *